(12) United States Patent
Ramsay et al.

(10) Patent No.: US 9,072,305 B2
(45) Date of Patent: Jul. 7, 2015

(54) HERBICIDAL FORMULATIONS

(75) Inventors: Julia Lynne Ramsay, Bracknell (GB); David Stock, Bracknell (GB); Gordon Alstair Bell, Bracknell (GB); Claudio Screpanti, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 396 days.

(21) Appl. No.: 13/254,354

(22) PCT Filed: Mar. 4, 2010

(86) PCT No.: PCT/GB2010/000385
§ 371 (c)(1),
(2), (4) Date: Dec. 5, 2011

(87) PCT Pub. No.: WO2010/100424
PCT Pub. Date: Sep. 10, 2010

(65) Prior Publication Data
US 2012/0071323 A1    Mar. 22, 2012

Related U.S. Application Data

(60) Provisional application No. 61/158,089, filed on Mar. 6, 2009.

(51) Int. Cl.
*A01N 57/20* (2006.01)
*A01N 37/38* (2006.01)
*A01N 25/02* (2006.01)
*A01N 57/12* (2006.01)
*A01N 41/06* (2006.01)
*A01N 25/30* (2006.01)

(52) U.S. Cl.
CPC ............... *A01N 57/20* (2013.01); *A01N 41/06* (2013.01); *A01N 25/30* (2013.01)

(58) Field of Classification Search
CPC .......... A01N 7/20; A01N 41/06; A01N 25/30
USPC .................................. 504/128, 206, 316, 362
See application file for complete search history.

(56) References Cited

U.S. PATENT DOCUMENTS

| | | | |
|---|---|---|---|
| 5,565,409 A | 10/1996 | Sato et al. | |
| 5,888,934 A * | 3/1999 | Townson et al. | 504/206 |
| 2003/0096708 A1 | 5/2003 | Agbaje et al. | |
| 2003/0104943 A1 | 6/2003 | Lennon et al. | |
| 2005/0192196 A1 | 9/2005 | Hutton, III et al. | |

FOREIGN PATENT DOCUMENTS

| | | |
|---|---|---|
| WO | WO 9909822 A1 * | 3/1999 |
| WO | WO 03094614 A1 * | 11/2003 |
| WO | 2004021790 | 3/2004 |

OTHER PUBLICATIONS

Gimenez, A.E., Annual grass control by glyphosate plus bentazon, chlorimuron, fomesafen, or imazethapyr, [online] Weed Technology, 1998, vol. 12, Issue 1 [Retrieved on Aug. 9, 2013]. Retrieved from the Internet: <http://www.cabdirect.org/abstracts/19982302747.html;jsessionid=416D20CCB24744240A1DB4C3531DDA6D#>, Abstract.*
Mueller, Thomas C.,Comparison of Glyphosate Salts (Isopropylamine, Diammonium, and Potassium) and Calcium and Magnesium Concentrations on the Control of Various Weeds, 2006, Weed Technology, vol. 20, pp. 164-171.*
U.S. Appl. No. 13/254,329, Restriction Requirement dated Mar. 15, 2013.
U.S. Appl. No. 13/254,329, Office Action dated Jun. 6, 2013.
U.S. Appl. No. 13/254,329, Final Office Action dated Jun. 16, 2014.

* cited by examiner

*Primary Examiner* — Abigail Fisher
*Assistant Examiner* — Andriae M Holt
(74) *Attorney, Agent, or Firm* — James Cueva

(57) ABSTRACT

The invention includes an aqueous compatibilized herbicidal formulation. In typical embodiments, formulations comprise a diammonium salt of glyphosate and a sodium salt of fomesafen. The invention also includes storage and transport systems containing formulation embodiments. The invention also includes methods inhibiting unwanted plant growth.

12 Claims, No Drawings

HERBICIDAL FORMULATIONS

This application is a 371 of International Application No. PCT/GB2010/000385 filed Mar. 4, 2010, which claims priority to US 61/158089 filed Mar. 6, 2009, the contents of which are incorporated herein by reference.

TECHNICAL FIELD

The present invention relates to aqueous formulations comprising at least two water-soluble electrolytic herbicides, typically at an increased concentration, and to methods of using such formulations to control unwanted weeds.

BACKGROUND

Glyphosate is a well characterized herbicide used to inhibit the growth of unwanted plants, such as grasses and weeds. Briefly, glyphosate is a non-selective systemic herbicide that prevents the synthesis of essential amino acids. Glyphosate is commonly used in the form of a salt, for example, potassium, trimethylsulphonium, isopropylamine, sodium, ammonium, diammonium, dimethylamine and triethanolamine as well as mixtures of these salts.

Glyphosate is often sold as concentrated salt or acid formulations configured to be diluted for application. For example, Touchdown Total® herbicide (Syngenta) is a commercial preparation of glyphosate in its potassium salt form, containing 500 grams of glyphosate (acid equivalent) per liter of water. Touchdown Total® herbicide is typically diluted in water to create a concentration suitable for application. Herbicidal application rates, in terms of the glyphosate acid equivalent may vary depending on, for example, species, age, stress, time of year, crop rotation, biotype, etc., but common rates include 560 g a.e./ha, 1120 g a.e./ha, and 1680 g a.e./ha.

The use and importance of glyphosate has increased in recent years because a variety of crop plants have been genetically transformed or selected to exhibit resistance to glyphosate. For example, glyphosate tolerant corn, glyphosate tolerant cotton and glyphosate tolerant soybeans may be treated with glyphosate with little risk of crop damage, resulting in increased yields due to decreased weed competition. Despite such benefits, one problem associated with the increased use of glyphosate is the development of glyphosate resistant weeds. Glyphosate resistant weeds can develop through natural selection in the field, as biotypes exhibiting some level of resistance outcompete herbicide-susceptible biotypes. Herbicide resistance is conferred to subsequent generations, where it may undergo additional selective pressure. The result is a weed population that can survive otherwise lethal doses of herbicide and negatively impact crop yield. One way to reduce the development and spread of glyphosate resistant weeds is to administer at least one other herbicide in addition to glyphosate to inhibit the glyphosate resistant weeds.

Mixes of two or more herbicides are commonly prepared by the grower in a process known as tank mixing. In tank mixing, typically, two or more concentrated formulations are dissolved, emulsified and/or suspended in a larger volume of water. One tank mix useful, for example, for treating or preventing glyphosate resistant weeds is prepared by tank mixing Touchdown Total® herbicide with Flexstar® herbicide (Syngenta). Flexstar® herbicide is a commercial preparation of fomesafen in its sodium salt form. Fomesafen is a known herbicide used to inhibit unwanted plant growth, and is typically used for post-emergence control of weeds, e.g., broad leaved weeds, in soybean plants. Fomesafen has the following structure, in acid form:

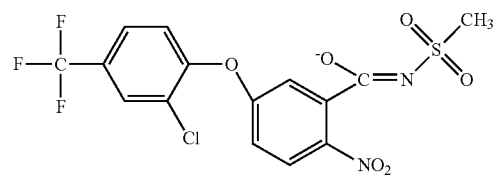

In addition to being useful for controlling and preventing resistant weed biotypes, herbicidal mixes are also useful for treating wild type weeds, for example, when a variety of different weeds are growing together or when trying to reduce the application rates of specific active ingredients. Mixing, however, is sometimes problematic.

For example, even in dilute tank mixes, compatibility between glyphosate and other herbicides is sometimes difficult to achieve. Further, when higher concentrations of glyphosate and another electrolytic herbicide are prepared, as when trying to make commercial premixes, the likelihood of compatibility problems is greatly increased. For example, in concentrated commercial mixes containing glyphosate and another electrolytic herbicide, phase separation, formation of solid precipitates, or other formulation failures can occur. Additionally, in some instances, tank mixing may result in crop phytotoxicity and/or herbicide antagonism or reduced weed control efficacy. Further, in some instances, herbicide mixes may formulate initially, but might not be suitable for storage and transport.

Various embodiments of the invention are directed to various combinations of these, and additional, problems.

SUMMARY

Applicants, to their surprise, discovered that compatibilized formulations comprising a diammonium salt of glyphosate and a sodium salt of fomesafen could be prepared at significantly higher concentrations than mixtures of other salts of these active ingredients. Formulations of the instant invention are thus useful as premixes or premixed commercial products. Formulations of the instant invention are particularly useful as concentrated premixes, which are typically configured to be diluted to create other concentrations prior to application. Premixes can be readily formulated with minimal risk of active ingredient incompatibility or antagonism, providing improvements in storage, transport, and application. Formulations of the invention are also particularly useful as components in storage and transport systems. Somewhat similarly, application concentrations formed from premix formulations of the invention are readily prepared with minimal risk of phase separation, precipitation, or antagonism.

The above, and additional, advantages are discussed in the detailed description section of the specification. Additional advantages are also apparent based on the teachings contained therein. Throughout the specification, unless otherwise noted, the amounts of glyphosate and fomesafen are provided on an acid equivalent (a.e.) basis. Concentration, unless otherwise noted, is given in weight/volume %, typically as g a.e./L or g/L.

By way of summary, in some embodiments, the invention includes aqueous compatibilized formulations. In one such embodiment, a formulation comprises a diammonium salt of glyphosate and a sodium salt of fomesafen.

In other embodiments, the invention includes an aqueous compatibilized formulation configured as a premix. In one such embodiment, a formulation comprises about 50 to about 400 g a.e./L of a diammonium salt of glyphosate and about 20 to about 400 g a.e./L of a sodium salt of fomesafen.

In other embodiments, the invention includes aqueous compatibilized formulations having a glyphosate-to-fomesafen acid equivalent ratio of at least 1:1.

Other embodiments include storage and shipping systems. In one such embodiment, a system comprises a container ranging in capacity from about 0.1 L to about 200 L. A compatibilized aqueous pesticidal formulation is located in the container. The formulation is typically concentrated. In one embodiment, the formulation comprises about 100 to about 400 g a.e./L of a diammonium salt of glyphosate and about 20 to about 400 g a.e./L of a sodium salt of fomesafen.

Other embodiments include methods of inhibiting the growth of an unwanted plant. In one such embodiment, the method includes applying a formulation to the plant. The formulation comprises a diammonium salt of glyphosate and a sodium salt of fomesafen. In another embodiment, the method includes diluting the formulation prior to application and applying the diluted concentration to the unwanted plant in an amount sufficient to inhibit plant growth.

The above summary was intended to summarize certain embodiments of the present invention. Formulations, systems, and methods of the present invention, including additional embodiments, will be set forth in more detail, along with examples demonstrating efficacy, in the figures and detailed description below. It will be apparent, however, that the detailed description is not intended to limit the present invention, the scope of which should be properly determined by the appended claims.

DETAILED DESCRIPTION

The inventors have surprisingly discovered that formulations comprising specifically selected salts of glyphosate and fomesafen, when used together, allow for a significant increase in compatibilized formulation concentration. As such, formulations of the instant invention are particularly useful as premixes and concentrated premixes configured to be diluted to create other application concentrations.

"Acid equivalent" or "a.e.", as used herein, means the theoretical yield of parent acid from a herbicidally active ingredient that has been formulated as a derivative (e.g. a salt, and esters, or an amine).

"Compatibilized", as used herein, means not exhibiting phase separation when stored at 25° C. for one week. Preferably the compositions do not exhibit phase separation when stored at 25° C. for one week and do not form crystals of the active herbicidal ingredient when stored at −5° C. for 24 hours.

"Concentrated", as used herein related to formulations, means a formulation has a combined concentration of a glyphosate salt and a fomesafen salt of at least 150 g a.e./L.

"Electrolytic", as used herein, means capable of creating an aqueous solution containing free ions that behaves as an electrically conductive medium.

"Water-soluble", as used herein, means having a solubility in deionized water at 20° C. sufficient to enable the water-soluble agrochemical electrolyte to be dissolved completely in the aqueous phase of a composition of the invention at the desired concentration. Preferred water-soluble active ingredients useful in the present invention have a solubility in deionized water at 20° C. of not less than about 10,000 mg/l, more preferably not less than about 100,000 mg/l. Where an active ingredient compound is referred to herein as being water-soluble, but the compound itself is known not to be water-soluble as defined immediately above, as is the case with glyphosate, it will be understood that the reference applies to water-soluble derivatives, more particularly water-soluble salts, of the compound.

In typical embodiments, the invention comprises an aqueous compatibilized formulation comprising a diammonium salt of glyphosate and a sodium salt of fomesafen.

As used herein, the diammonium salt of glyphosate can comprise a mixture of ammonium salts and diammonium salts. In many embodiments, the diammonium salt will be the dominant salt form, meaning the diammonium form will be at least about 50%, 55%, 60%, 65%, 70%, 75%, 80%, 85%, 90%, or about 95%, by weight, of the glyphosate acid equivalent.

The formulations of the present invention may contain additional surfactants and adjuvants to increase stability of the concentrated formulation and/or increase efficacy of the applied product. Surfactants and adjuvants suitable for use in the present invention include those known in the art, for example, anionic surfactants such as alkybenzene sulfonates, alkyl naphthalene sulfonates, alcohol sulfonates, ether sulfates, alkyl sulfosuccinates, sulfonated naphthalene/formaldehyde condensates, lignosulfonates, polycarboxylates, olefin sulfonates, phosphate ethoxylates, tristyrylphenol phosphates and sulfates and taurates; non-ionic surfactants such as alkylphenol ethoxylates, tristyrylphenol ethoxylates, alcohol ethoxylates, alkyl ester ethoxylates, aliphatic acid ethoxylates, sorbitan esters and ethoxylates, castor oil ethoxylates, amine ethoxylates, polymeric surfactants, for example block copolymers and comb/graft copolymers, organosilicones and cetylenic diols; cationic surfactants such as quaternary ammonium compounds, amine salts, amine oxides and amine ethoxylates; and amphoteric surfactants.

Particularly preferred adjuvants for use in the compositions of the present invention include alkyl polyglycosides.

Alkyl polyglycosides (APG) suitable for use in the present invention have formula (I):

$$R_1O(R_2O)_b(Z)_a \qquad (I)$$

$R_1$ is straight or branched chain alkyl or alkenyl group having from about 4 to about 30 carbon atoms. $R_1$ is typically a straight or branched chain $C_{4-22}$ alkyl or alkenyl group, more typically a $C_{8-11}$ alkyl group. $R_2$ is an alkylene having from about 2 to about 4 carbon atoms. $R_2$ is typically ethylene or propylene, more typically ethylene. b is 0 to about 100. b is typically 0 to about 12, more typically 0. Z is a saccharide residue having about 5 to about 6 carbon atoms. Z may be glucose, mannose, fructose, galasctose, talose, gulose, altrose, allose, apiose, gallose, idose, ribose, arabinose, xylose, lyxose, or a mixture thereof. Z is typically glucose. 'a' is an integer from 1 to about 6, typically from 1 to about 3, more typically from 1 to about 2.

Typical compounds of formula (I) are compounds of formula (II):

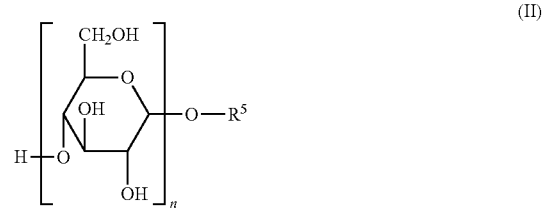

where n is the degree of polymerization and is from 1 to 3, preferably 1 or 2, and $R^5$ is a branched or straight chain alkyl group having from 4 to 18 carbon atoms or a mixture of alkyl groups having from 4 to 18 carbon atoms. Most typically, the alkyl polyglycoside comprises an alkyl group containing 8-10 carbon atoms and has an average degree of polymerization of 1.7; an alkyl group containing 9-11 carbon atoms and has an average degree of polymerization of 1.3 to 1.6; or a-mixture thereof APG also includes embodiments, such as those described above, which have been anionically or cationically modified.

Exemplary alkyl polyglycosides include APG® 325 (Cognis Corporation, Cincinnati, Ohio) (an alkyl polyglycoside in which the alkyl group contains 9 to 11 carbon atoms and has an average degree of polymerization of 1.6), PLANTAREN® 2000 (Cognis Corporation, Cincinnati, Ohio) (an alkyl polyglycoside in which the alkyl group contains 8 to 16 carbon atoms and has an average degree of polymerization of 1.4), PLANTAREN® 1300 (Cognis Corporation, Cincinnati, Ohio) (an alkyl polyglycoside in which the alkyl group contains 12 to 16 carbon atoms and has an average degree of polymerization of 1.6), AGNIQUE® PG 8107 (Cognis Corporation, Cincinnati, Ohio) (an alkyl polyglycoside in which the alkyl group contains 8 to 10 carbon atoms and has an average degree of polymerization of 1.7), AGNIQUE® PG 9116 (Cognis Corporation, Cincinnati, Ohio) (an alkyl polyglycoside in which the alkyl group contains 9 to 11 carbon atoms and has an average degree of polymerization of 1.6) and AGNIQUE® PG 8105 (Cognis Corporation, Cincinnati, Ohio) (an alkyl polyglycoside in which the alkyl group contains 8 to 10 carbon atoms and has an average degree of polymerization of 1.5).

Concentrations may vary from embodiment to embodiment. Typically, the diammonium salt of glyphosate is present at about 50 to about 400 g a.e./L, at about 100 to about 400 g a.e./L, at about 150 to about 400 g a.e./L, at about 200 to about 400 g a.e./L, at about 250 to about 400 g a.e./L, at about 300 to about 400 g a.e./L, and at about 350 to about 400 g a.e./L. More typically, the diammonium salt of glyphosate is present at about 150 to about 350 g a.e./L, and about 250 to about 350 g a.e./L. Typically, the salt of fomesafen is present at about 20 to about 400 g a.e./L, at about 50 to about 400 g a.e./L, at about 100 to about 400 g a.e./L, at about 150 to about 400 g a.e./L, at about 200 to about 400 g a.e./L, at about 250 to about 400 g a.e./L, at about 300 to about 400 g a.e./L, and at about 350 to about 400 g a.e./L. More typically the salt of fomesafen is present at about 50 to 150 g a.e./L.

Concentrated formulations according to the invention include any combination of the above concentrations of a diammonium salt of glyphosate and a sodium salt of fomesafen to create a combined concentration of at least 200 g a.e./L. For example, a concentrated formulation includes a diammonium salt of glyphosate at about 200 g a.e./L and a sodium salt of fomesafen at about 50 g a.e./L. An additional example of a concentrated formulation includes a diammonium salt of glyphosate at about 150 g a.e./L and a sodium salt of fomesafen at about 150 g a.e./L. Numerous examples are readily apparent.

Oftentimes formulations of the invention are prepared at desired ratios, for example, a desired glyphosate (acid equivalent)-to-fomesafen (acid equivalent) ratio. Typical ratios include, for example, 9:1, 6:1, 3:1 and 1:1.

In an exemplary embodiment, a formulation comprises, by weight percent, about 100 to about 400 g a.e./L of the diammonium salt of glyphosate and about 20 to about 400 g a.e./L of the sodium salt of fomesafen.

In another embodiment, a formulation comprises, by weight percent, about 150 to about 400 g a.e./L of a diammonium salt of glyphosate; about 20 to about 400 g a.e./L of a sodium salt of fomesafen; and about 50 to about 300 WL of at least one alkyl polyglycoside.

Formulations of the invention may also include, by weight/volume %, about 1% to about 15% of a hydrotrope, e.g., salts of xylene sulphonic acid, salts of cumene sulphonic acid or salts of toluene sulphonic acid. Typically, the hydrotrope will be sodium xylene sulphonate (SXS). In some embodiments, hydrotropes may be desirable to further increase concentration loading. Additionally, hydrotropes may also be desirable for lowering viscosity for improved handling, dilution, and application.

Formulations of the invention may also include other inert additives. Such additives include thickeners, flow enhancers, wetting agents, antifoaming agents, biocides, buffers, lubricants, fillers, drift control agents, deposition enhancers, adjuvants, evaporation retardants, freeze protecting agents, insect attracting odor agents, stabilizing metal salts or hydroxides, UV protecting agents, fragrances, and the like. The thickener may be a compound that is soluble or able to swell in water, such as, for example, polysaccharides of xanthans (e.g., anionic heteropolysaccharides), alginates, guars or celluloses such as RHODOPOL® 23 (Xanthan Gum)(Rhodia, Cranbury, N.J.); synthetic macromolecules, such as polyethylene glycols, polyvinyl pyrrolidones, polyvinyl alcohols, polycarboxylates, bentonites, montmorillonites, hectonites, or attapulgites. The freeze protecting agent may be, for example, ethylene glycol, propylene glycol, glycerol, diethylene glycol, saccharose, water-soluble salts such as sodium chloride, sorbitol, triethylene glycol, tetraethylene glycol, urea, or mixtures thereof. Representative anti-foam agents are silica, polydialkylsiloxanes, in particular polydimethylsiloxanes, fluoroaliphatic esters or perfluoroalkylphosphonic/perfluoroalkylphosphonic acids or the salts thereof and mixtures thereof. Preferred are polydimethylsiloxanes, such as Dow Corning® Antifoam A or Antifoam B. Representative biocides include 1,2-benzisothiazolin-3-one, available as PROXEL® GXL (Arch Chemicals).

As noted above, formulations of the present invention are advantageous because they have increased acid equivalent concentrations of glyphosate and fomesafen. Formulations of the present invention are also advantageous because they achieve weed control at levels similar to tank mixes of commercial glyphosate and fomesafen products.

Other embodiments of the invention include storage and shipping systems. Typical storage and shipping systems comprise a container ranging in capacity from about 0.1 L to about 200 L and a compatibilized aqueous herbicidal pesticidal formulation located in the container. Typically, the formulation will be concentrated. The container may include the standard 2.5 gallon (9.46 L) containers widely used in the United States, which typically take the form of jugs or flasks with a replaceable screw-cap. These containers are generally designed for single use and are typically not returned to the supplier when empty, instead being disposed of by the end user in accordance with local agricultural chemical container disposal guidelines, procedures, regulations or laws. Commonly, a plurality of these small containers are packaged within a single box and a plurality of such boxes are shipped on a pallet. During shipment, the small containers (usually within boxes on pallets) can be disposed in an enclosed volume such as provided by a rail boxcar or road truck, the hold of a ship or aircraft, or a modular box container adapted for transport by road, rail and water. Larger single-use containers, ranging in capacity up to about 200 liters, for example about 50 to about 200 liters, are commonly in the form of drums, and can be shipped in an enclosed volume as described above, one or more per pallet or unpalleted.

Formulations of the invention also can be distributed in a large refillable container sometimes known as a bulk or minibulk tank, which typically has an integral pump or connector for an external pump to permit transfer of liquid. Bulk or minibulk tanks having a capacity of about 200 to about 2000 liters or more are typically returned to the supplier when empty and are commonly shipped on a pallet.

Formulations used in the storage and transport system include any of the formulations described above. In one embodiment, the formulation located inside the container comprises about 200 to about 350 g a.e./L of a diammonium salt of glyphosate and about 50 to about 300 g a.e./L of a sodium salt of fomesafen. In one embodiment, the formulation will include about 50 to about 300 g/L of at least one alkyl polyglycoside.

Formulations according to the invention may be used for pre-emergence application or post-emergence application.

Other embodiments of the invention include methods of inhibiting the growth of an unwanted plant. Examples of unwanted plants include monocot and dicot weeds, including velvetleaf, pigweed, giant ragweed, common lambsquarters, ivyleaf morningglory, annual grasses, etc. The term plant refers to all physical parts of a plant, including seeds, seedlings, saplings, roots, tubers, stems, stalks, foliage and fruits.

Methods of the present invention are suitable especially for combating and/or preventing unwanted plants among crops of useful plants. Methods of the invention are also suitable combating and/or preventing unwanted plants physically distinct from crops or crop areas, e.g., non-crop lands, along unplanted roadsides or under power lines.

Preferred crops of useful plants include cotton, dry beans, snap beans and soybeans.

Crops are to be understood as also including those crops which have been rendered tolerant to herbicides or classes of herbicides (e.g. ALS-, GS-, EPSPS-, PPO-, ACCase, Auxin- and HPPD-inhibitors) by conventional methods of breeding or by genetic engineering. An example of a crop that has been rendered tolerant to imidazolinones, e.g. imazamox, by conventional methods of breeding is Clearfield® summer rape (canola)(BASF). Examples of crops that have been rendered tolerant to herbicides by genetic engineering methods include e.g. glyphosate- and glufosinate-tolerant maize varieties commercially available under the trade names RoundupReady® (Monsanto) and LibertyLink® (Bayer Crop Science). When the compositions of the present invention are used post-emergent over crops, the crops will typically be selected from those crops tolerant, either by genetic engineering methods, artificial selection, or naturally, to the herbicides present in the compositions.

Crops are also to be understood as being those that have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by Bacillus thuringiensis soil bacteria. Examples of toxins, or transgenic plants able to synthesise such toxins, are described in EP-A-451 878, EP-A-374 753, WO 93/07278, WO 95/34656, WO 03/052073 and EP-A-427 529. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavor).

Other useful plants include turf grass for example in golf-courses, lawns, parks and roadsides, or grown commercially for sod, and ornamental plants such as flowers or bushes.

Crop areas are areas of land on which the cultivated plants are already growing or in which the seeds of those cultivated plants have been sown, and also areas of land on which it is intended to grow those cultivated plants.

In one embodiment, the method includes applying a formulation to the plant. The formulation comprises a diammonium salt of glyphosate and a sodium salt of fomesafen.

In another embodiment, the method includes diluting the formulation in a volume of water prior to application. The amount of water needed to form dilutions is ascertainable to one of ordinary skill in the art, being dependent on, for example, the initial formulation concentration and the desired application concentration and volume. Dilutions will most typically be performed to create concentrations sufficient to inhibit plant growth. The application rate will depend upon the particular type of pests to be controlled, the degree of control required, and the timing and method of application.

Application may be by any of the variety of ways known to those skilled in the art. Typically, application will be by spraying.

The improvements in compatibility obtained by the compositions of the present invention are further illustrated in the examples below.

EXAMPLES

In order that those skilled in the art will be better able to practice the invention, the following examples are given by way of illustration and not by way of limitation. In the following examples, as well as elsewhere in the specification and claims, temperatures are in degrees Celsius, the pressure is atmospheric and all parts are by weight/volume percent acid equivalent, unless otherwise clearly indicated.

Table 1 compares the maximum compatibilized concentrations achievable with ammonium/diammonium salt-matched formulations to invention formulations at ambient temperature for four weeks.

TABLE 1

| 2:1 Ratio | | 3:1 Ratio | | 4:1 Ratio | |
| --- | --- | --- | --- | --- | --- |
| Salt-Matched | Invention | Salt-Matched | Invention | Salt-Matched | Invention |
| 240 g/L diammonium glyphosate | 240 g/L diammonium glyphosate | 280 g/L diammonium glyphosate | 280 g/L diammonium glyphosate | 320 g/L diammonium glyphosate | 320 g/L diammonium glyphosate |
| 120 g/L ammonium fomesafen | 120 g/L sodium fomesafen | 93 g/L ammonium fomesafen | 93 g/L sodium fomesafen | 80 g/L ammonium fomesafen | 80 g/L sodium fomesafen |

Each formulation also included Agnique PG 8107 at 214 g/L; All formulations were a clear solution. "Maximum" values are approximations based replicates prepared at 30 or 40 g a.e./L diammonium glyphosate intervals.

Table 2 illustrates the unexpected increase in maximum compatibilized concentrations achievable with invention formulations relative to salt-matched formulations after storage at −5° C. for four weeks.

TABLE 2

| 2:1 Ratio | | 3:1 Ratio | | 4:1 Ratio | |
|---|---|---|---|---|---|
| Salt-Matched | Invention | Salt-Matched | Invention | Salt-Matched | Invention |
| 210 g/L diammonium glyphosate 105 g/L ammonium fomesafen | 240 g/L diammonium glyphosate 120 g/L sodium fomesafen | 210 g/L diammonium glyphosate 70 g/L ammonium fomesafen | 240 g/L diammonium glyphosate 80 g/L sodium fomesafen | 210 g/L diammonium glyphosate 53 g/L ammonium fomesafen | 280 g/L diammonium glyphosate 70 g/L sodium fomesafen |

Each formulation also included Agnique PG 8107 at 214 g/L; All formulations were a clear solution. "Maximum" values are approximations based replicates prepared at 30 or 40 g a.e./L diammonium glyphosate intervals.

Table 3 illustrates the incompatibility of potassium glyphosate with sodium or ammonium fomesafen. The advantages of sodium fomesafen over ammonium fomesafen are seen on −5° C. storage as described in Table 2 above. The results from Table 3 are based on mixtures prepared without APG present. Mixtures of glyphosate with potassium fomesafen were not prepared due to the limited water solubility of potassium fomesafen.

TABLE 3

| | | | Result | pH |
|---|---|---|---|---|
| Another salt selection | 120 g/l potassium glyphosate (base to acid ratio of 1.1:1 approx) | 60 g/l sodium fomesafen | Separation of liquid and solid phases from the aqueous phase | 4.8 |
| Another salt selection | 120 g/l potassium glyphosate (base to acid ratio of 1.1:1 approx) | 60 g/l ammonium fomesafen | Separation of liquid and solid phases from the aqueous phase | 4.7 |
| Another salt selection | 120 g/l potassium glyphosate (base to acid ratio of 1.6:1 approx) | 60 g/l ammonium fomesafen | Separation of liquid and solid phases from the aqueous phase | 5.8 |
| Another salt selection | 120 g/l diammonium glyphosate | 60 g/l ammonium fomesafen | Clear solution | 6.2 |
| Invention | 120 g/l diammonium glyphosate | 60 g/l sodium fomesafen | Clear solution | 6.3 |

Table 4 further illustrates various compatibility profiles of the invention (diammonium glyphosate and sodium fomesafen)

TABLE 4

| Glyphosate:fomesafen ratio | Concentrations giving one phase solution | Concentrations giving two phase solutions |
|---|---|---|
| 9:1** | <=137 g/L gly + 15 g/L fom** | >=155 g/L gly + 17 g/L fom** |
| 6:1** | <=133 g/L gly + 22 g/L fom** | >=150 g/L gly + 25 g/L fom** |
| 3:1 | <=135 g/L gly + 45 g/L fom | >=155 g/L gly + 52 g/L fom |
| 1:1 | <=117 g/L gly + 117 g/L fom | >=140 g/L gly + 140 g/L fom |
| 1:2 | <=110 g/L gly + 220 g/L fom | >=120 g/L gly + 240 g/L fom |
| 1:3 | <=87 g/L gly + 262 g/L fom | |

**formation of a white crystalline precipitate with after 24 hours at ambient temperature.

Table 5 also illustrates concentration ranges for different mixture ratios over which incompatibility arises. For the 9:1 ratio, the mixture becomes incompatible at a glyphosate concentration somewhere between 137 g/L and 155 g/L. For the 6:1 ratio, the mixture becomes incompatible at a glyphosate concentration somewhere between 133 g/L and 150 g/L. For the 3:1 ratio, the mixture becomes incompatible at a glyphosate concentration somewhere between 135 g/L and 155 g/L. For the 1:1 ratio, the mixture becomes incompatible at a glyphosate concentration somewhere between 117 g/L and 14 g/L.

Table 5 illustrates a further improvement in invention compatibility achieved by the use of APG (Agnique PG 8107).

TABLE 5

| 9:1 Ratio | 3:1 Ratio | 1:2 Ratio |
|---|---|---|
| 315 g/L diammonium glyphosate | 270 g/L diammonium glyphosate | 150 g/L diammonium glyphosate |
| 35 g/L sodium fomesafen | 90 g/L sodium fomesafen | 300 g/L sodium fomesafen |
| 214 g/L Agnique PG 8107 | 214 g/L Agnique PG 8107 | 214 g/L Agnique PG 8107 |
| Water to 1 L | Water to 1 L | Water to 1 L |
| Clear brown solution* | Clear brown solution | Clear brown solution |

*additionally no white precipitate forms with the 9:1 ratio after 24 hours at ambient temperature Surprisingly, for each mixture ratio, it was discovered that APG allowed for even higher compatibilized glyphosate concentrations than the formulations in Table 4.

Numerous characteristics and advantages have been set forth in the foregoing description, together with details of structure and function. The novel features are pointed out in the appended claims. The disclosure, however, is illustrative only, and changes may be made in detail, especially in matters of shape, size, and arrangement of parts, within the principle of the invention, to the full extent indicated by the broad general meaning of the terms in which the general claims are expressed.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Applicants typically account for such variation by using the term "about" to modify a particular number or range. Moreover, all ranges disclosed herein are to be understood to encompass any and all subranges subsumed therein, and every number between the end points. For example, a stated range of "1 to 10 g/L" or should be considered to include any and all subranges between (and inclusive of) the minimum value of 1 g/L and the maximum value of 10 g/L; that is, all subranges beginning with a minimum value of 1 g/L or more, e.g. 1 g/L to 6.1 g/L, and ending with a maximum value of 10 g/L or less, e.g., 5.5 g/L to 10 g/L, as well as all ranges beginning and ending within the end points, e.g. 2 to 9 g/L, 3 to 8 g/L, 3 to 9 g/L, 4 to 7 g/L, and finally to each number 1 g/L, 2 g/L, 3 g/L, 4 g/L, 5 g/L, 6 g/L, 7 g/L, 8 g/L, 9 g/L and 10 g/L contained within the range.

It is further noted that, as used in this specification, the singular forms "a," "an," and "the" include plural referents unless expressly and unequivocally limited to one referent.

What is claimed is:

1. An aqueous compatibilized herbicidal formulation comprising:
about 150 to about 400 g a.e./L of a diammonium salt of glyphosate;
about 20 to about 400 g a.e./L of a sodium salt of fomesafen; and
about 50 to about 300 g/L of at least one alkyl polyglycoside having formula (I)

$$R_1O(R_2O)_b(Z)_a \qquad (I)$$

wherein:
$R_1$ is straight or branched chain alkyl or alkenyl group having from about 4 to about 30 carbon atoms;
$R_2$ is an alkylene having from about 2 to about 4 carbon atoms;
b is 0 to about 100;
Z is a saccharide residue having about 5 to about 6 carbon atoms; and
'a' is an integer from 1 to about 6.

2. The formulation of claim 1, wherein 'a' is about 1 to about 2.

3. The formulation of claim 1, further comprising, by weight/volume %, about 1% to about 15% of at least one hydrotrope.

4. The formulation of claim 3, wherein the at least one hydrotrope is chosen from a salt of xylene sulphonic acid, a salt of cumene sulphonic acid, and a salt of toluene sulphonic acid.

5. The formulation of claim 3, wherein the at least one hydrotrope includes sodium xylene sulphonate.

6. The formulation of claim 1, wherein the formulation has a glyphosate-to-fomesafen ratio from about 3:1 to about 4:1.

7. A storage and shipping system comprising:
a container having a capacity of about 0.1 L to about 200 L; and
an aqueous pesticidal formulation located in the container, the concentrated formulation comprising
about 150 to about 400 g a.e./L of a diammonium salt of glyphosate,
about 20 to about 400 g a.e./L of at least one salt of fomesafen, and
about 50 to about 300 g/L of at least one alkyl polyglycoside having formula (I)

$$R_1O(R_2O)_b(Z)_a \qquad (I)$$

wherein:
$R_1$ is straight or branched chain alkyl or alkenyl group having from about 4 to about 30 carbon atoms;
$R_2$ is an alkylene having from about 2 to about 4 carbon atoms;
b is 0 to about 100;
Z is a saccharide residue having about 5 to about 6 carbon atoms; and
'a' is an integer from 1 to about 6.

8. The system of claim 7, wherein the container capacity is about 0.1 L to about 20 L.

9. A method of inhibiting the growth of an unwanted plant, the method comprising
applying a formulation to the plant, the formulation comprising
about 150 to about 400 g a.e./L of a diammonium salt of glyphosate;
about 20 to about 400 g a.e./L of a sodium salt of fomesafen; and
about 50 to about 300 g/L of at least one alkyl polyglycoside having formula (I)

$$R_1O(R_2O)_b(Z)_a \qquad (I)$$

wherein:
$R_1$ is straight or branched chain alkyl or alkenyl group having from about 4 to about 30 carbon atoms;
$R_2$ is an alkylene having from about 2 to about 4 carbon atoms;
b is 0 to about 100;
Z is a saccharide residue having about 5 to about 6 carbon atoms; and
'a' is an integer from 1 to about 6.

10. The method of claim 9, further including diluting the formulation in a volume of water prior to applying.

11. The method of claim 9, wherein the unwanted plant is among crops in a crop area.

12. The method of claim 11 wherein the crop comprises glyphosate tolerant cotton or glyphosate tolerant soybeans.

* * * * *